United States Patent
Makino

(10) Patent No.: US 12,053,146 B2
(45) Date of Patent: Aug. 6, 2024

(54) ENDOSCOPE SYSTEM

(71) Applicant: HOYA CORPORATION, Tokyo (JP)

(72) Inventor: Takao Makino, Tokyo (JP)

(73) Assignee: HOYA CORPORATION, Tokyo (JP)

(*) Notice: Subject to any disclaimer, the term of this patent is extended or adjusted under 35 U.S.C. 154(b) by 499 days.

(21) Appl. No.: 17/436,742

(22) PCT Filed: Sep. 1, 2020

(86) PCT No.: PCT/JP2020/033030
§ 371 (c)(1),
(2) Date: Sep. 7, 2021

(87) PCT Pub. No.: WO2021/059889
PCT Pub. Date: Apr. 1, 2021

(65) Prior Publication Data
US 2022/0192470 A1 Jun. 23, 2022

(30) Foreign Application Priority Data
Sep. 27, 2019 (JP) .................................. 2019-177859

(51) Int. Cl.
*A61B 1/00* (2006.01)
*A61B 1/045* (2006.01)
(Continued)

(52) U.S. Cl.
CPC .... *A61B 1/000094* (2022.02); *A61B 1/00045* (2013.01); *A61B 1/045* (2013.01);
(Continued)

(58) Field of Classification Search
CPC .......... A61B 1/000094; A61B 1/00045; A61B 1/045; A61B 1/0684; G06T 7/0012;
(Continued)

(56) References Cited

U.S. PATENT DOCUMENTS

2006/0050966 A1* 3/2006 Nishimura .............. G06T 7/136
 382/209
2008/0281154 A1* 11/2008 Gono ................... A61B 1/0669
 600/109
(Continued)

FOREIGN PATENT DOCUMENTS

JP 2004-181096 7/2004
JP 2015-223249 12/2015
(Continued)

OTHER PUBLICATIONS

International Search Report issued in International Bureau of WIPO Patent Application No. PCT/JP2020/033030, dated Nov. 17, 2020, along with an English translation thereof.

*Primary Examiner* — John P Leubecker
*Assistant Examiner* — Jae Woo
(74) *Attorney, Agent, or Firm* — GREENBLUM & BERNSTEIN P.L.C.

(57) ABSTRACT

An endoscope system comprising: a light source device configured to emit illumination light; an electronic endoscope; a processor that includes an image processing unit; and a monitor. The image processing unit includes: a detection unit configured to generate a first blood vessel detection image and a second blood vessel detection image; a separation unit configured to separate the first blood vessel detection image and the second blood vessel detection image into a shallow blood vessel image and a deep blood vessel image; a feature amount calculation unit configured to calculate a shallow blood vessel feature amount regarding the shallow blood vessel image and a deep blood vessel feature amount regarding the deep blood vessel image; and an evaluation unit configured to calculate severity of a lesion of a biological tissue by using the shallow blood vessel feature amount and the deep blood vessel feature amount.

14 Claims, 5 Drawing Sheets

(51) Int. Cl.
*A61B 1/06* (2006.01)
*G06T 7/00* (2017.01)
*G06T 7/136* (2017.01)

(52) U.S. Cl.
CPC .......... *A61B 1/0676* (2013.01); *A61B 1/0684* (2013.01); *G06T 7/0012* (2013.01); *G06T 7/136* (2017.01); *G06T 2207/10068* (2013.01); *G06T 2207/30096* (2013.01); *G06T 2207/30101* (2013.01)

(58) Field of Classification Search
CPC ........... G06T 7/136; G06T 2207/10068; G06T 2207/30096; G06T 2207/30101
See application file for complete search history.

(56) References Cited

U.S. PATENT DOCUMENTS

| | | | | |
|---|---|---|---|---|
| 2011/0112362 | A1* | 5/2011 | Minetoma | A61B 1/000094 600/109 |
| 2011/0237884 | A1* | 9/2011 | Saito | A61B 5/489 600/109 |
| 2011/0245642 | A1* | 10/2011 | Minetoma | A61B 1/0655 600/324 |
| 2012/0154565 | A1* | 6/2012 | Kaku | A61B 1/0638 348/68 |
| 2013/0289373 | A1* | 10/2013 | Yamamoto | A61B 5/1459 600/339 |
| 2014/0187881 | A1* | 7/2014 | Saito | A61B 1/0638 600/323 |
| 2016/0089011 | A1* | 3/2016 | Shiraishi | A61B 1/044 348/71 |
| 2018/0214004 | A1* | 8/2018 | Kamon | A61B 5/14552 |
| 2018/0218499 | A1 | 8/2018 | Kamon | |
| 2018/0279866 | A1* | 10/2018 | Makino | A61B 1/00009 |
| 2021/0133974 | A1 | 5/2021 | Makino | |

FOREIGN PATENT DOCUMENTS

| | | |
|---|---|---|
| JP | 2016-077756 | 5/2016 |
| WO | 2017/057572 | 4/2017 |
| WO | 2017/057573 | 4/2017 |
| WO | 2017/057680 | 4/2017 |
| WO | 2019/159435 | 8/2019 |

\* cited by examiner

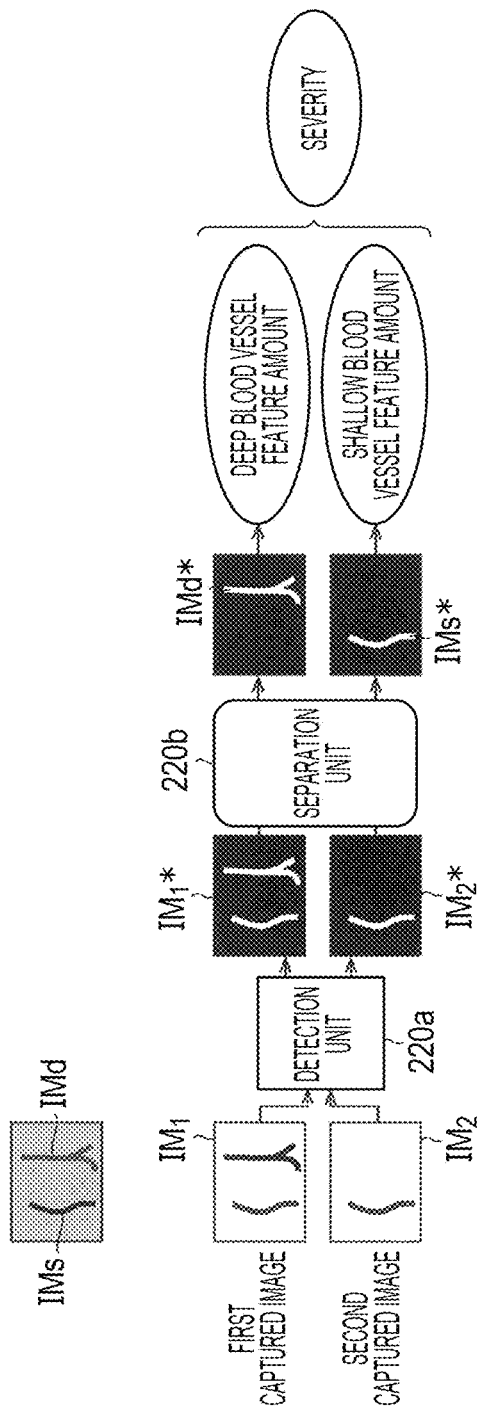

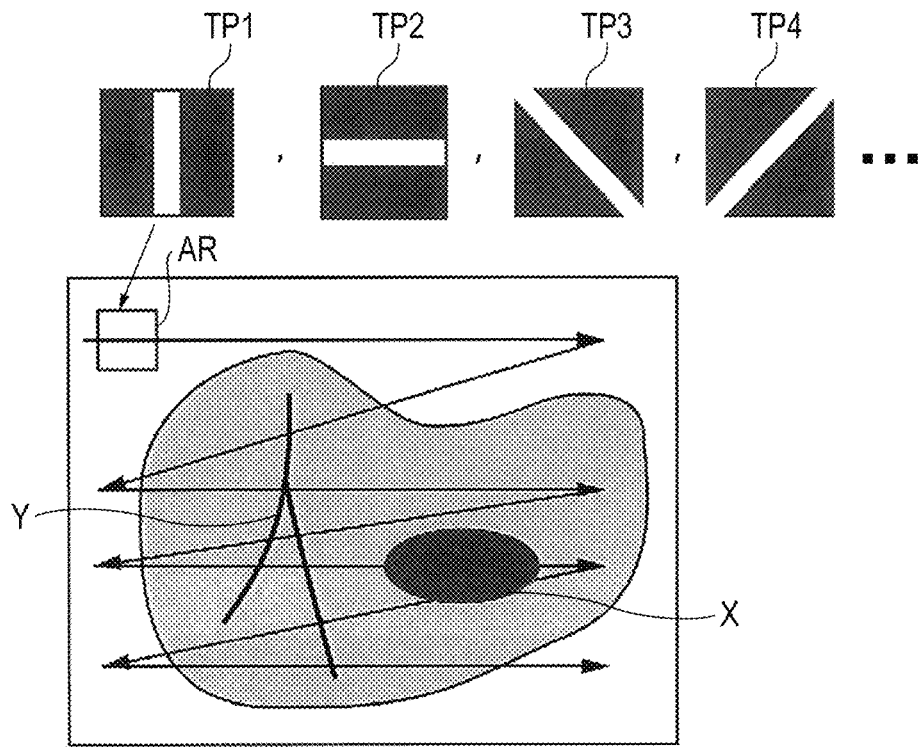

ENDOSCOPE SYSTEM

TECHNICAL FIELD

The present invention relates to an endoscope system for evaluating severity of a lesion of a biological tissue using an image of the biological tissue in a body cavity.

BACKGROUND ART

In a lesion area in a biological tissue, various levels of severities are present, from a red-colored inflammation due to a thinned and roughened mucosal layer of the biological tissue to an ulcer in which the mucosal layer and a lower layer thereof are partially lost. For example, an ulcer area of a lesion of an ulcerative colitis (UC) includes white moss or mucopus and is white, while an inflamed area includes edema or hemorrhagic and is reddish. The lesion area can be imaged and observed with an endoscope system.

However, it is necessary to undergo long-term training under a guidance of a skilled person in order for an operator to be able to distinguish between a normal portion and a lesion portion by a difference in color contained in an image of the endoscope. In addition, it is not easy for even a skilled operator to identify the lesion area by using a slight color difference, and careful work needs to be carried out. Therefore, it is preferable that the endoscope system provides an evaluation result obtained by objectively converting a degree of the lesion in the lesion area into a numerical value.

In contrast, an endoscope system is known which can stably calculate an evaluation value by suppressing fluctuations in the evaluation value of the inflamed area which are caused by brightness of the image, and can suppress a processing load in calculating the evaluation value (Patent Literature 1).

CITATION LIST

Patent Literature

Patent Literature 1: WO No. 2017/057680 A

SUMMARY OF INVENTION

Technical Problem

The endoscope system described above includes a light source device that irradiates an object with illumination light, an image acquisition unit that images reflected light from the object by an image sensor and acquires a color image including at least three or more color components, and an evaluation unit. The evaluation unit obtains an evaluation result regarding a target disease of each pixel on the basis of an angle formed by a line segment connecting a pixel corresponding point in a color plane of each pixel constituting the color image acquired by the image acquisition unit and a predetermined reference point set in the color plane and a reference axis having correlation with the target disease in the color plane defined by at least two color components among at least three or more color components. The reference axis is set to pass through a predetermined reference point. The reference axis is at least one of an axis having a correlation with a target disease in which an inflamed degree within the color plane has a predetermined value or smaller and an axis having a correlation with a target disease in which an inflamed degree has a predetermined value or greater within the color plane.

According to this configuration, the evaluation value can be stably calculated by suppressing fluctuations in the evaluation value which are caused by the brightness of the image, and a processing load in calculating the evaluation value can be suppressed.

However, the evaluation value required by the endoscope system is an evaluation value of the entire biological tissue including the blood vessel image. Depending on the type of lesion, a blood vessel image appearing as an object may change depending on the degree of progress of the lesion. For example, depending on the progression of the lesion, there may be less blood vessels visible on the surface of the biological tissue, and more blood vessels may be concentrated inside. However, in such a case, the evaluation value for evaluating the entire image does not sufficiently correspond to subjective evaluation results or histologic evaluation results by a doctor. The endoscope system cannot evaluate the severity of the lesion by distinguishing the blood vessel image appearing as the object from the image of the biological tissue other than the blood vessel and calculating the blood vessel feature amount.

Therefore, an object of the present invention is to provide an endoscope system capable of accurately evaluating the severity of a lesion by distinguishing a blood vessel image appearing in an image of an object from an image of a biological tissue other than the blood vessel and calculating a blood vessel feature amount when evaluating the severity of a lesion using an image of a biological tissue in a body cavity.

Solution to Problem

One aspect of the present invention is an endoscope system. The endoscope system includes:
  a light source device configured to emit illumination light;
  an electronic endoscope configured to image a biological tissue including a blood vessel in a body cavity illuminated with the illumination light;
  a processor that includes an image processing unit configured to calculate severity of a lesion of the biological tissue from an image of the biological tissue obtained by the electronic endoscope by using information of the image; and
  a monitor configured to display information on the severity.

The light source device is configured to emit, as at least the illumination light, first light and second light having a wavelength band on a shorter wavelength side than a wavelength band of the first light.

The image processing unit includes
  a detection unit configured to generate a first blood vessel detection image including an emphasized blood vessel image from a first captured image obtained by illumination with the first light, and further generate a second blood vessel detection image including an emphasized blood vessel image from a second captured image obtained by illumination with the second light, by using features of the blood vessel portion with which the blood vessel portion is able to be distinguished from the non-blood vessel portion,
  a separation unit configured to separate and take out, from the first blood vessel detection image and the second blood vessel detection image, the blood vessel images in the first blood vessel detection image and the second blood vessel detection image into a shallow blood vessel image and a deep blood vessel image as blood vessel images having different depth positions from a surface of the biological tissue, a feature data calculation unit configured to calculate a shallow blood vessel feature amount regarding the shallow blood vessel image and a deep blood vessel feature amount regarding the deep blood vessel image, and an evaluation unit configured to calculate the severity of a lesion of the biological tissue using at least the shallow blood vessel feature amount and the deep blood vessel feature amount.

It is preferable that the separation unit detects a region of the blood vessel image in the second blood vessel detection image as a region of the shallow blood vessel image, and detects the region of the deep blood vessel image by removing the detected region of the shallow blood vessel image from the region of the blood vessel image in the first blood vessel detection image to, thereby, detect the shallow blood vessel image and the deep blood vessel image.

It is preferable that the separation unit is configured to detect a region of the shallow blood vessel image according to whether or not each pixel value of an average detection image in which an average value of pixel values of corresponding pixels of the first blood vessel detection image and the second blood vessel detection image is a pixel value is equal to or greater than a preset first threshold value, detect a mixed region including a region of the shallow blood vessel image and a region of the deep blood vessel image according to whether or not each pixel value of the first captured image is equal to or greater than a preset second threshold value, and detect a region of the deep blood vessel image by removing the detected region of the shallow blood vessel image from the detected mixed region.

It is preferable that the separation unit is configured to obtain a pixel value of a corresponding region of the second captured image corresponding to the region of the shallow blood vessel image as a pixel value of the shallow blood vessel image and obtain a pixel value of a corresponding region of the first captured image corresponding to the region of the deep blood vessel image as a pixel value of the deep blood vessel image, and that the feature amount calculation unit is configured to calculate the shallow blood vessel feature amount and the deep blood vessel feature amount using the obtained pixel value of the shallow blood vessel image and the obtained pixel value of the deep blood vessel image.

An aspect of the present invention is an endoscope system. The endoscope system includes:

a light source device configured to emit illumination light;

an electronic endoscope configured to image a biological tissue including a blood vessel in a body cavity illuminated with the illumination light;

a processor that includes an image processing unit configured to calculate severity of a lesion of the biological tissue from an image of the biological tissue obtained by the electronic endoscope by using information of the image; and a monitor configured to display information on the severity.

The light source device is configured to emit, as at least the illumination light, first light and second light having a wavelength band on a shorter wavelength side than a wavelength band of the first light.

The image processing unit includes a separation unit configured to separate and extract, from a first captured image obtained by illumination with the first light and a second captured image obtained by illumination with the second light, a first image portion including a shallow blood vessel image as a part of an image and a second image portion including a deep blood vessel image as a part of an image among the shallow blood vessel image and the deep blood vessel image with different depth positions from a surface of the biological tissue, a detection unit configured to generate the shallow blood vessel image and the deep blood vessel image from the first image portion and the second image portion by using features of the blood vessel portion with which the blood vessel portion is able to be distinguished from the non-blood vessel portion, a feature data calculation unit configured to calculate a value of a shallow blood vessel feature amount regarding the shallow blood vessel image and a value of a deep blood vessel feature amount regarding the deep blood vessel image, and an evaluation unit configured to calculate the severity of a lesion of the biological tissue using at least the value of the shallow blood vessel feature amount and the value of the deep blood vessel feature amount.

It is preferable that the separation unit is configured to create the first image portion according to whether or not each pixel value of an average image in which an average value of pixel values of corresponding pixels of the captured image and the second captured image is a pixel value is equal to or greater than a preset first threshold value, detect a mixed image including the shallow blood vessel image and the deep blood vessel image as a part of images according to whether or not each pixel value of the first captured image is a preset second threshold value, and remove the generated first image portion from the detected mixed image to create the second image portion.

It is preferable that the detection unit is configured to detect a blood vessel image emphasized by template matching using a feature shape of a blood vessel in which the blood vessel extends linearly.

It is preferable that the evaluation unit is configured to calculate the severity by adding or subtracting a value obtained by multiplying the value of the shallow blood vessel feature amount by a coefficient and a value obtained by multiplying the value of the deep blood vessel feature amount by a coefficient.

It is preferable that the evaluation unit is configured to perform predictive evaluation on the severity from a value of the shallow blood vessel feature amount and a value of the deep blood vessel feature amount in the living tissue which are calculated by the feature amount calculation unit by using a prediction model obtained by performing machine learning on a correspondence relationship between the shallow blood vessel feature amount and the deep blood vessel feature amount and the evaluation on the severity of the lesion of the living tissue, with information on the evaluation of each of a plurality of reference images for which evaluation on the severity prepared in advance has been determined, and the shallow blood vessel feature amount and the deep blood vessel feature amount calculated from the reference image using the image processing unit as machine learning data.

It is preferable that the light source device is configured to emit one light, which includes each of the first light and the second light as a light component, as the illumination light, and that the electronic endoscope is configured to separate an object image of a biological tissue into the first captured image and the second captured image using an optical filter.

It is preferable that the first light includes a first absorption peak wavelength among a plurality of absorption peak wavelengths of hemoglobin in a wavelength band, and that the second light includes, in a wavelength band, a second absorption peak wavelength on a shorter wavelength side than the first absorption peak wavelength among the plurality of absorption peaks.

It is preferable that the wavelength band of at least one of the first light and the second light does not include any of the plurality of absorption peak wavelengths of the hemoglobin.

It is preferable that the wavelength band of the second light includes a wavelength having an absorption coefficient of the hemoglobin greater than a maximum value of an absorption coefficient of the hemoglobin in the wavelength band of the first light.

It is preferable that the light source device is configured to emit third light having a wavelength band on a longer wavelength side than a wavelength band of the first light.

Advantageous Effects of Invention

According to the endoscope system described above, it is possible to accurately evaluate the severity of the lesion by distinguishing the blood vessel image appearing in the image of the object from the image of the biological tissue other than the blood vessel image and calculating the blood vessel feature amount.

BRIEF DESCRIPTION OF DRAWINGS

FIG. 3 is a diagram illustrating an example of a flow of detecting a blood vessel image and separating a deep blood vessel image and a shallow blood vessel image performed by the image processing unit included in the endoscope system according to the embodiment.

FIG. 4 is a diagram illustrating an example of a method of detecting a blood vessel image performed by the image processing unit included in the endoscope system according to the embodiment.

FIG. 5 is a diagram illustrating an example of a filter coefficient of a spatial filter used by the image processing unit included in the endoscope system according to the embodiment.

DESCRIPTION OF EMBODIMENTS

Figure 1:
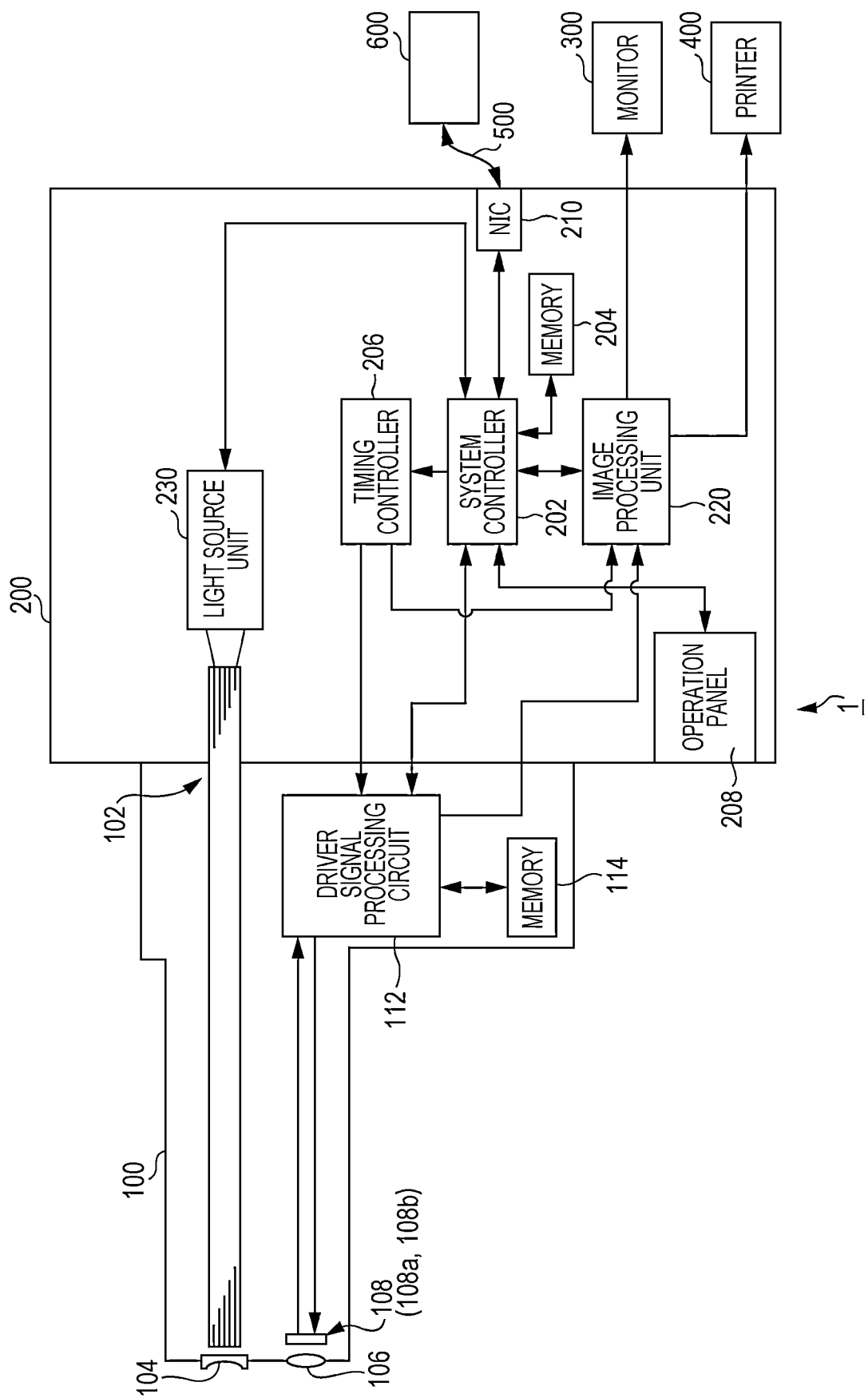
FIG. 1 is a block diagram illustrating an example of a configuration of an endoscope system according to an embodiment.

Hereinafter, before describing an endoscope system according to an embodiment of the present invention with reference to the drawings, a concept of an endoscope system will be described.

A progress of a lesion in a biological tissue causes various changes in the biological tissue. A conventional endoscope system calculates a feature amount of a lesion by using a pixel value of an image captured using white light as illumination light, and evaluates severity of the lesion. As described above, since a blood vessel image is also included in the captured image when the biological tissue is captured, the blood vessel image is also integrally used for evaluating the severity together with the image of the lesion other than the blood vessel image of the biological tissue. Such evaluation results may not sufficiently correspond to evaluation results by doctors or histologic evaluation results. Therefore, the endoscope system of one embodiment detects a blood vessel image and evaluates the severity of the lesion by using the blood vessel image. At this time, the captured blood vessel also varies depending on a wavelength band range of the illumination light. For example, in the illumination light having a wavelength band of a short wavelength, blood vessels in the vicinity of a surface of the biological tissue are imaged, and in the illumination light having a wavelength band of a long wavelength, the blood vessels in the vicinity of the surface of the biological tissue and blood vessels at a certain depth compared to the vicinity of the surface are imaged. Therefore, the biological tissue is imaged by dividing the illumination light into the illumination light having the long wavelength band and the illumination light having the short wavelength band or using the illumination light including the light component having the long wavelength band and the light component having the long wavelength band. Therefore, in the endoscope system of one embodiment, a first captured image of the biological tissue illuminated with the illumination light having the long wavelength band or the first captured image of the biological tissue in the wavelength band corresponding to the light component having the long wavelength band is acquired, and a second captured image of the biological tissue illuminated with the illumination light having the short wavelength band or the second captured image of the biological tissue in the wavelength band corresponding to the light component having the short wavelength band is acquired. In this case, a light source device that emits the illumination light emits first light and second light having a wavelength band on a shorter wavelength side than the wavelength band of the first light.

In the illumination light, since a blood vessel image is clearly obtained by light absorption of hemoglobin in blood in a blood vessel, it is preferable, as an example, that the wavelength band of the illumination light or the wavelength band of the light component of the illumination light includes a light absorption peak wavelength of hemoglobin. Therefore, in this case, as the illumination light, the first light including a first absorption peak wavelength among the plurality of absorption peak wavelengths of hemoglobin in the wavelength band and the second light including a second absorption peak wavelength shorter than the first peak wavelength among the plurality of absorption peaks of hemoglobin in the wavelength band are used. For example, the wavelength band of the first light does not include the second absorption peak wavelength, and the wavelength band of the second light does not include the first absorption peak wavelength. The endoscope system can obtain the first captured image and the second captured image by using each of the first light and the second light as the illumination light. Furthermore, the endoscope system can obtain the first captured image and the second captured image by separating the object image of the biological tissue obtained by illuminating each of the first light and the second light with the illumination light as the light component using the optical filter.

Furthermore, in another example related to the first light and the second light, as long as a shallow blood vessel image and a deep blood vessel image having different depth positions from the surface of the biological tissue can be separated from the first captured image and the second captured image, the wavelength band of at least one of the first light and the second light does not include any absorption peak wavelength of the plurality of absorption peak wavelengths of hemoglobin.

Furthermore, in another example related to the first light and the second light, the wavelength band of the second light includes a wavelength having an absorption coefficient of hemoglobin larger than a maximum value of the absorption coefficient of hemoglobin in the wavelength band of the first light. As a result, the shallow blood vessel image and the deep blood vessel image can be reliably separated from the first captured image and the second captured image.

The endoscope system generates, from the two first captured images and second captured images, a first blood vessel detection image including an emphasized blood vessel image and further generates a second blood vessel detection image including an emphasized blood vessel image from the second captured image, by using features of a blood vessel portion with which the blood vessel portion can be distinguished from a non-blood vessel portion.

Furthermore, the endoscope system separates a blood vessel image in the first blood vessel detection image and a blood vessel image in the second blood vessel detection image from the first blood vessel detection image and the second blood vessel detection image into the shallow blood vessel image and the deep blood vessel image as blood vessel images having different depth positions from the surface of the biological tissue.

Further, the endoscope system calculates a shallow blood vessel feature amount related to the separated shallow blood vessel image and a deep blood vessel feature amount related to the separated deep blood vessel image, and calculates the severity of the lesion of the biological tissue by using at least the shallow blood vessel feature amount and the deep blood vessel feature amount.

Note that, after the blood vessel image emphasized from the first captured image and the second captured image is detected, the blood vessel image is separated into the shallow blood vessel image and the deep blood vessel image, but after the blood vessel image is separated from the first captured image and the second captured image into an image portion including the shallow blood vessel image as a part of the image and an image portion including the deep blood vessel image as a part of the image, the blood vessel image emphasized from the separated image portion is detected, so the shallow blood vessel image and the deep blood vessel image can be obtained.

As described above, the endoscope system obtains the shallow blood vessel image and the deep blood vessel image as the blood vessel images having different depth positions from the surface of the biological tissue using the first light and the second light having different wavelength bands, and uses the shallow blood vessel feature amount and the deep blood vessel feature amount calculated from these blood vessel images for calculation of the severity of the lesion of the biological tissue, so it is possible to accurately evaluate the severity of the lesion of the lesion compared to a case where the evaluation is performed using only illumination light which is white light as in the related art. The severity thus evaluated corresponds well to subjective evaluation results (for example, MAYO endoscopic subscore) by doctors or histologic evaluation results.

FIG. 1 is a block diagram illustrating a configuration of an endoscope system 1 according to an embodiment of the present embodiment. As illustrated in FIG. 1, the endoscope system 1 includes an electronic scope 100, an electronic endoscope processor 200, a monitor 300, and a printer 400.

The electronic endoscope processor 200 includes a system controller 202 and a timing controller 206. The system controller 202 executes various programs stored in a memory 204 and integrally controls the entire endoscope system 1. In addition, the system controller 202 changes various settings of the endoscope system 1 in accordance with an instruction of a user (operator or assistant) which is input to an operation panel 208. The timing controller 206 outputs a clock pulse for adjusting an operation timing of each unit to each circuit in the endoscope system 1.

The electronic endoscope processor 200 includes a light source unit (light source device) 230 that supplies illumination light to the electronic scope 100. Although not illustrated, for example, the light source unit 230 includes a high-luminance lamp that emits white illumination light by receiving drive power from a lamp power supply, for example, such as a xenon lamp, a metal halide lamp, a mercury lamp, or a halogen lamp. The light source unit 230 is configured such that the illumination light emitted from the high-luminance lamp alternately generates and emits the first light and the second light having different wavelength bands from each other by an optical filter (not illustrated), is condensed by a condenser lens (not illustrated), and is then incident on an incident end of a light carrying bundle (LCB) 102 that is a bundle of optical fibers of the electronic scope 100 via a dimming device (not illustrated).

Alternatively, the light source unit 230 includes a light emitting diode that emits the first light and second light having different wavelength bands. The first light and the second light are alternately emitted from the light emitting diode, or the first light and the second light emitted from the light emitting diode are synthesized and emitted as one illumination light using an optical element such as a dichroic mirror. The light source unit 230 is configured such that the emitted first light and second light are condensed by a condensing lens (not illustrated) and then incident on an incident end of the light carrying bundle (LCB) 102 of the electronic scope 100. A laser diode can be used instead of the light emitting diode. Since the light emitting diode and the laser diode have features such as low power consumption and a low heat generation amount, compared to other light sources, there is an advantage in that a bright image can be acquired while suppressing the power consumption or the heat generation amount.

In an example illustrated in FIG. 1, the light source unit 230 is provided by being incorporated in the electronic endoscope processor 200, but may be provided in the endoscope system 1 as a device separate from the electronic endoscope processor 200. In addition, the light source unit 230 may be provided in a distal tip of the electronic scope 100 to be described later. In this case, the LCB 102 that guides the illumination light is unnecessary.

The illumination light incident from the incident end into the LCB 102 is propagated in the LCB 102 and is emitted from an emission end of the LCB 102 arranged in the distal tip of the electronic scope 100, and is applied to an object via a light distribution lens 104. The reflected light from the object forms an optical image on a light receiving surface of an image sensor 108 via an objective lens 106.

The image sensor 108 is, for example, a single-plate color charge-coupled device (CCD) image sensor in which various filters such as an infrared (IR) cut filter 108*a* and a Bayer-arranged color filter 108*b* are arranged on the light receiving surface, and generates primary color signals of red (R), green (G), and blue (B) according to the optical image formed on the light receiving surface. Instead of the single-plate color CCD image sensor, a single-plate color complementary metal oxide semiconductor (CMOS) image sensor can also be used. In this way, the electronic scope 100 uses the image sensor 108 to image a biological tissue inside a body cavity.

The electronic scope 100 includes a driver signal processing circuit 112 provided in a connection portion thereof. The driver signal processing circuit 112 performs predetermined signal processing such as color interpolation or matrix calculation on the primary color signal input from the image sensor 108 to generate an image signal (luminance signal Y, and color difference signals Cb and Cr). Further, the driver signal processing circuit 112 outputs the generated image signal to the image processing unit 220 of the electronic endoscope processor 200. In addition, the driver signal processing circuit 112 accesses the memory 114, and reads specific information of the electronic scope 100. For example, the specific information of the electronic scope 100 recorded in the memory 114 includes the number of pixels or sensitivity of the image sensor 108, a frame rate with which the electronic scope 100 is operable, and a model number. The driver signal processing circuit 112 outputs the specific information read from the memory 114 to the system controller 202.

The system controller 202 in the electronic endoscope processor 200 performs various calculations on the basis of the information stored in the memory 204 and the unique information transmitted from the electronic scope 100, and generates a control signal. The system controller 202 controls an operation and a timing of each circuit inside the electronic endoscope processor 200 by using the generated control signal so that processing suitable for the electronic scope 100 connected to the electronic endoscope processor 200 is performed.

The timing controller 206 supplies a clock pulse to the driver signal processing circuit 112, the image processing unit 220, and the light source unit 230 in accordance with timing control of the system controller 202. The driver signal processing circuit 112 performs driving control of the image sensor 108 at a timing synchronized with the frame rate of the video image processed on the electronic endoscope processor 200 side in accordance with the clock pulses supplied from the timing controller 206.

Under the control of the system controller 202, the image processing unit 220 generates a video signal for displaying an endoscope image on a monitor, based on the image signal input from the driver signal processing circuit 112, and outputs the video signal to the monitor 300. Further, the image processing unit 220 obtains the severity indicating the degree of the lesion of the biological tissue by a numerical value from the captured image of the biological tissue obtained by the electronic scope 100. In addition, the image processing unit 220 generates a blood vessel detection image or a captured image obtained at the time of performing quantification processing for obtaining the severity. The image processing unit 220 generates a video signal for displaying information on the evaluation result and a color map image on the monitor, and outputs the video signal to the monitor 300. As a result, an operator can obtain information on the severity of the lesion of the biological tissue of interest through the image displayed on the display screen of the monitor 300. If necessary, the image processing unit 220 outputs the color map image and the information on the evaluation result to the printer 400.

The electronic endoscope processor 200 is connected to a server 600 via a network interface card (NIC) 210 and a network 500. The electronic endoscope processor 200 can download information (for example, electronic medical record information of a patient or information of the operator) regarding an endoscopic examination from the server 600. For example, the downloaded information is displayed on the display screen of the monitor 300 or the operation panel 208. In addition, the electronic endoscope processor 200 uploads an endoscopic examination result (endoscope image data, an examination condition, an image analysis result, or an operator's opinion) to the server 600, so it is possible to store the endoscopic examination result in the server 600.

Figure 2:
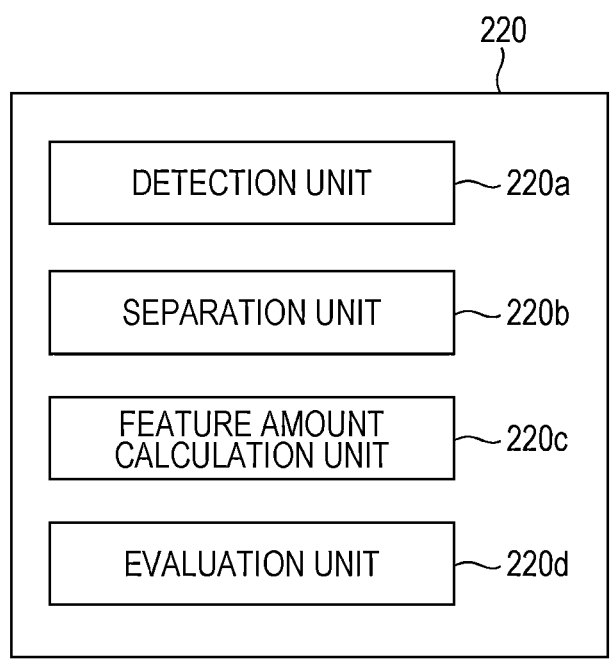
FIG. 2 is a diagram illustrating an example of a configuration of an image processing unit of the endoscope system according to the embodiment.

FIG. 2 is a diagram illustrating an example of a part of the configuration of the image processing unit 220 included in the endoscope system 1 of one embodiment. A constituent part of the image processing unit 220 illustrated in FIG. 2 relates to a part that performs numerical processing of numerically indicating the degree of pathology in order to calculate the severity of the pathology of the biological tissue. Although not illustrated, the image processing unit 220 includes a processing main body portion that generates a video signal for displaying an endoscope image or the like on a monitor and performs image processing for outputting the video signal to the monitor 300.

As illustrated in FIG. 2, the image processing unit 220 includes at least a detection unit 220a, a separation unit 220b, a feature amount calculation unit 220c, and an evaluation unit 220d.

The detection unit 220a generates the first blood vessel detection image in which the blood vessel image is detected from the first captured image obtained by the illumination with the first light by using the features of the blood vessel portion with which the blood vessel portion can be distinguished from the non-blood vessel portion. Furthermore, the detection unit 220a generates the second blood vessel detection image in which the blood vessel image is detected from the second captured image obtained by the illumination with the second light. A detection method by the detection unit 220a will be described later.

From the first blood vessel detection image and the second blood vessel detection image, the separation unit 220b separates the blood vessel images in the first blood vessel detection image and the second blood vessel detection image into the shallow blood vessel image and the deep blood vessel image as the blood vessel images having different depth positions from the surface of the biological tissue, and extracts the images. A separation method by the separation unit 220b will be described later.

The feature amount calculation unit 220c calculates the shallow blood vessel feature amount related to the shallow blood vessel image and the deep blood vessel feature amount related to the deep blood vessel image. The shallow blood vessel feature amount and the deep blood vessel feature amount will be described later.

The evaluation unit 220d calculates the severity of the lesion of the biological tissue using at least the shallow blood vessel feature amount and the deep blood vessel feature amount. The calculation of the severity will be described later.

FIG. 3 is a diagram illustrating an example of a flow of detecting the blood vessel image and separating the deep blood vessel image and the shallow blood vessel image performed by the image processing unit 220.

The detection of the blood vessel image performed by the detection unit 220a is performed using the first captured image obtained by the illumination with the first light and the second captured image obtained by the illumination with the second light. In this case, the second light has a wavelength band on a shorter wavelength side than the wavelength band of the first light. The wavelength band of the first light includes, as an example, a first absorption peak wavelength among a plurality of absorption peak wavelengths of hemoglobin in the wavelength band, and the wavelength band of the second light includes, as an example, a second absorption peak wavelength on a shorter wavelength side than the first peak wavelength in the wavelength band. That is, the first light and the second light are narrowband light. For example, the hemoglobin has a large absorption peak at 400 to 450 nm (Soret absorption band of a porphyrin ring), and also has an absorption peak at 520 to 590 nm (Q band of a porphyrin ring). Thus, the wavelength band of the first light includes a wavelength of 520 to 590 nm and the wavelength band of the second light includes a wavelength of 400 to 450 nm. For example, the wavelength band of the first light does not include a wavelength of 400 to 450 nm, and the wavelength band of the second light does not include a wavelength of 520 to 590 nm. Light having a wavelength of 400 to 450 nm is light in a blue region, and light having a wavelength of 520 to 590 nm is light in a green region.

Therefore, as illustrated in FIG. 3, a first captured image $IM_1$ obtained by the illumination with the first light includes a blood vessel image $IM_s$ in the vicinity of the surface of the biological tissue and a blood vessel image $IM_d$ at a certain depth compared to the vicinity of the surface. The second captured image $IM_2$ obtained by the illumination with the second light includes only the blood vessel image $IM_s$ in the vicinity of the surface of the biological tissue.

The detection unit 220a detects the first blood vessel detection image $IM_1^*$ and the second blood vessel detection image $IM_2^*$ from the first captured image $IM_1$ and the second captured image $IM_2$.

As another example of the illumination light, the wavelength band of the second light includes a wavelength having an absorption coefficient of hemoglobin larger than the maximum value of the absorption coefficient of hemoglobin in the wavelength band of the first light. In this case, the wavelength band of the first light is, for example, 520 to 590 nm, and the wavelength band of the second light is, for example, 430 to 470 nm.

As another example of the illumination light, the wavelength band of at least one of the first light and the second light does not include any absorption peak wavelength of the plurality of absorption peak wavelengths of hemoglobin. The wavelength band of the first light is, for example, 590 to 610 nm, and the wavelength band of the second light is, for example, 450 to 470 nm. In this case, neither the wavelength band of the first light nor the wavelength band of the second light includes an absorption peak wavelength.

In this manner, various wavelength bands can be set for the first light and the second light.

FIG. 4 is a diagram illustrating an example of a method of detecting a blood vessel image. The detection of the blood vessel image is performed using features of the blood vessel portion with which the blood vessel portion can be distinguished from the non-blood vessel portion.

For example, the detection unit 220a obtains a matching degree indicating a degree of correlation between the shape of an examination target area AR of a part of the image of the biological tissue and each of the linear shapes of a plurality of templates TP1 to TP4. Further, the detection unit 220a obtains a value of the highest matching degree among the matching degrees corresponding to the plurality of templates TP1 to TP4 as the certainty of the blood vessel region in the examination target area AR. The templates TP1 to TP4 are configured to include pixels, and the templates TP1 to TP4 have a plurality of line shapes having different extending directions. In the templates TP1 to TP4, each pixel has a pixel value in accordance with each line shape. As illustrated in FIG. 4, the examination target areas AR are moved sequentially from an end of the image along an arrow while overlapping each other, so the degree of correlation between the pixel value of the image inside the examination target area AR and the value of the pixel corresponding to each of the templates TP1 to TP4 is obtained. According to the embodiment, the templates TP1 to TP4 have four line shapes extending in four different extending directions as shapes featured by the blood vessel. The templates TP1 to TP4 have a value for each pixel corresponding to a white region and a black region which are illustrated in FIG. 4. Therefore, according to the embodiment, the matching degree is a correlation coefficient between the pixel value of the templates TP1 to TP4 and the corresponding pixel evaluation value of the examination target area AR. In addition, according to the embodiment, the matching degree may be a total value obtained by multiplying each filter coefficient by an image value of the corresponding pixel of the examination target area AR, by using the values for each pixel of the templates TP1 to TP4 as filter coefficients of a spatial filter.

The highest matching degree having the greatest value in the matching degrees calculated for the respective templates TP1 to TP4 is assigned to a central pixel of the examination target area AR, as the value indicating the certainty of the blood vessel region.

FIG. 5 is a view illustrating an example of the filter coefficient when the template TP1 is used as the spatial filter. As illustrated in FIG. 5, the template TP1 has a shape in which a straight line extends in an upward-downward direction in the drawing. In FIG. 5, as an example, the template TP1 forms the spatial filter of 5×5 pixels. In this case, ⅕ is assigned as the filter coefficient to the pixels of the portion extending in the linear shape, and −1/20 is assigned as the filter coefficient to the other pixels.

When a total value obtained by multiplying each of the filter coefficients by the image value of the corresponding pixel of the examination target area AR is calculated as the matching degree, in a case where all of the pixel values of the examination target area AR are values the same as each other, the matching degree is zero. On the other hand, when the examination target area AR includes an image of the blood vessel extending in a stripe streak in the upward-downward direction, the matching degree increases. As the value of the matching degree is greater, it can be described that the examination target area AR includes the image that approximates the template TP1. Therefore, the matching degree is calculated for each of the templates TP1 to TP4, and the highest matching degree having the greatest value in the calculated matching degrees is assigned to a central pixel of the examination target area AR, as the certainty of the blood vessel. That is, the value of the certainty of the blood vessel area is given to the central pixel of the examination target area AR. In this way, the first blood vessel detection image $IM_1^*$ and the second blood vessel detection image $IM_2^*$ including the blood vessel image emphasized by the value of the certainty of the blood vessel region can be obtained.

In this manner, the blood vessel image detection unit 220a obtains the first blood vessel detection image $IM_1^*$ and the second blood vessel detection image $IM_2^*$ from the first captured image $IM_1$ and the second captured image $IM_2$ obtained by the illumination with the first light and the second light by using the features of the blood vessel portion with which the blood vessel portion can be distinguished from the non-blood vessel portion. In the case of obtaining the pixel values of the blood vessel images in the first blood vessel detection image $IM_1^*$ and the second blood vessel detection image $IM_2^*$, the blood vessel image detection unit 220a creates a mask image by assigning 1 to the pixel values at which the pixel values of the first blood vessel detection image $IM_1^*$ and the second blood vessel detection image $IM_2^*$ are equal to or greater than a predetermined threshold value, and assigning 0 to the pixel values of the other regions. Furthermore, the blood vessel image detection unit 220a can obtain the pixel values of the blood vessel images in the first blood vessel detection image $IM_1^*$ and the second blood vessel detection image $IM_2^*$ by calculating a product of the pixel values of the mask image and the corresponding pixels of the first captured image $IM_1$ and the second captured image $IM_2$.

In the examples of the blood vessel detection illustrated in FIGS. 4 and 5 described above, the template matching using the feature shape of the blood vessel is used, but the blood vessel detection is not limited to the template matching using the feature shape of the blood vessel. For example, a blood vessel detection method using a band-pass filter or a line segment detection method based on the degree of vector concentration can also be used. For example, the blood vessel can be detected by generating an edge image of the blood vessel by applying a band pass filter to a color component image of the green region. Note that an edge extraction method using a bandpass filter is a known technique. In addition, it is also possible to detect a blood vessel using a vector concentration degree as described in WO 2012/002012.

The blood vessel image highlighted in the first blood vessel detection image $IM_1^*$ and the second blood vessel detection image $IM_2^*$ generated by the detection unit 220a is separated into a deep blood vessel image $IM_d^*$ and a shallow blood vessel image $IM_s^*$ by the separation unit 220b.

Figure 6A:
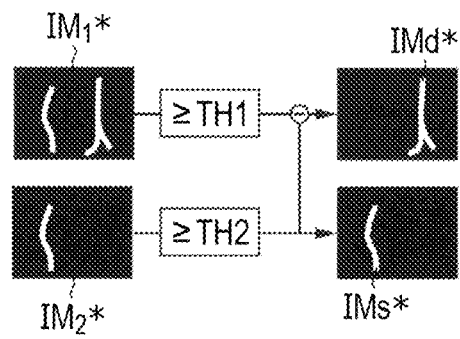
FIGS. 6(a) to 6(c) are diagrams illustrating an example of separation of a blood vessel image performed by the endoscope system according to the embodiment.
Figure 6B:
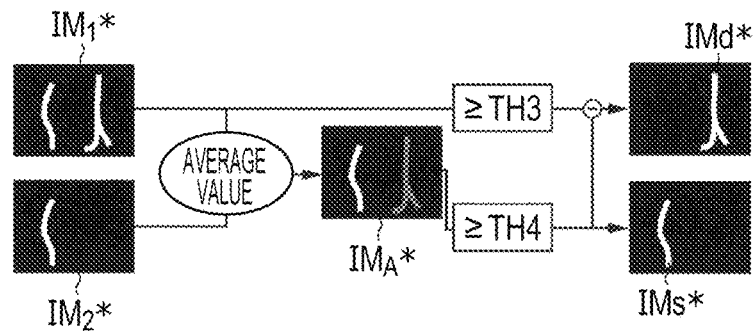
Figure 6C:
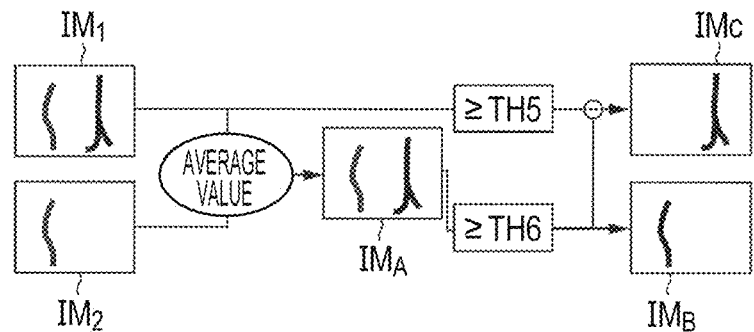

FIGS. 6(a) to 6(c) are diagrams for describing an example of separation of a blood vessel image performed by the endoscope system according to an embodiment.

In the separation illustrated in FIG. 6(a), in a case where the pixel value of the second blood vessel detection image $IM_2^*$ which is generated from the second captured image $IM_2$ obtained by imaging the shallow blood vessel in the vicinity of the surface of the biological tissue and is the emphasized blood vessel is greater than or equal to a predetermined threshold value TH2, the separation unit 220b assigns a value 1 to this pixel and assigns a value 0 to the other pixels. As a result, the separation unit 220b obtains the region of the pixel value of value 1 of the binarized image as the region of the shallow blood vessel image $IM_s^*$. Furthermore, in a case where the pixel value of the first blood vessel detection image $IM_1^*$ generated from the first captured image $IM_1$ obtained by imaging the shallow blood vessel in the vicinity of the surface of the biological tissue and the deep blood vessel at a certain depth compared to the vicinity of the surface and in which the blood vessel image is emphasized is equal to or greater than the predetermined threshold value TH1, a value 1 is assigned to this pixel, and a value 0 is assigned to the other pixels. As a result, the separation unit 220b obtains the remaining region obtained by removing the previously obtained region of the shallow blood vessel image $IM_s$ from the region of the pixel value of value 1 of the binarized image, that is, the region of the blood vessel image as the region of the deep blood vessel image $IM_d^*$.

In the separation illustrated in FIG. 6(b), the separation unit 220b creates an average detection image $IM_A^*$ in which an average value of the pixel value of the second blood vessel detection image $IM_2^*$ and the pixel value of the first blood vessel detection image $IM_1^*$ is set as a pixel value. The pixel value of the second blood vessel detection image $IM_2^*$ is generated from the second captured image $IM_2$ obtained by imaging the shallow blood vessel in the vicinity of the surface of the biological tissue, and is an image in which the blood vessel image is emphasized, and the first blood vessel detection image $IM_1^*$ is generated from the first captured image $IM_1$ obtained by imaging the shallow blood vessel in the vicinity of the surface of the biological tissue and the deep blood vessel at a certain depth compared to the vicinity of the surface and is an image in which the blood vessel image is emphasized. The separation unit 220b determines whether each pixel value of the average detection image $IM_A^*$ is greater than or equal to a preset threshold value TH4 (first threshold value), and detects a region of the pixel value greater than or equal to the threshold value TH4 as a region of the shallow blood vessel image $IM_s^*$.

Furthermore, the separation unit 220b detects a mixed region including a region of the shallow blood vessel image $IM_s^*$ and a region of the deep blood vessel image $IM_d^*$ depending on whether each pixel value of the first captured image $IM_1$ is equal to or greater than a threshold value TH3 (second threshold value) set in advance, and removes the previously detected region of the shallow blood vessel image from the detected mixed region. As a result, the separation unit 220b detects the region of the deep blood vessel image $IM_d^*$. That is, the separation unit 220b detects the remaining region obtained by removing the previously detected region of the shallow blood vessel image from the mixed region as the region of the deep blood vessel image $IM_d^*$.

In the separation illustrated in FIG. 6(c), the separation unit 220b creates an average image $IM_A$ having, as pixel values, an average value of pixel values of the second captured image $IM_2$ obtained by imaging the shallow blood vessel in the vicinity of the surface of the biological tissue and pixel values of the first captured image $IM_1$ obtained by imaging a shallow blood vessel in the vicinity of the surface of the biological tissue and a deep blood vessel at a position deeper than the vicinity of the surface to some extent. The separation unit 220b determines whether each pixel value of the average image $IM_A$ is equal to or larger than a preset threshold value TH6 (first threshold value), and creates a first image portion $IM_B$ including a region of pixel values equal to or larger than the threshold value TH6 as a part of the shallow blood vessel image.

Further, the separation unit 220b determines whether each pixel value of the average image $IM_A$ is greater than or equal to a preset threshold value TH5 (The threshold value TH5 is lower than the threshold value TH6.). The separation unit 220b detects a mixed image including a region having a pixel value equal to or greater than a threshold value TH5 (second threshold value) as a part of the shallow blood vessel image and the deep blood vessel image, and removes the previously created first image portion $IM_B$ from the detected mixed image (specifically, by subtracting the corresponding pixel value of the first image portion $IM_B$ previously created from the pixel value of the mixed image,)

to create a second image portion $IM_s$ including the deep blood vessel image as a part of the images.

The first image portion $IM_B$ and the second image portion $IM_C$ thus created are used in the detection unit 220a to generate the shallow blood vessel image $IM_s^*$ and the deep blood vessel image $IM_d^*$ by using features of the blood vessel portion with which the blood vessel portion can be distinguished from the non-blood vessel portion. That is, the example illustrated in FIG. 6(c) is used for a method of separating the shallow blood vessel image and the deep blood vessel image, and then emphasizing the blood vessel image using the features of the blood vessel portion with which the blood vessel portion can be distinguished from the non-blood vessel portion.

In the case of the example illustrated in FIG. 6(c), the separation unit 220b of the image processing unit 220 separates the first captured image $IM_1$ and the second captured image $IM_2$ into a first image portion $IM_B$ including the shallow blood vessel image $IM_s^*$ as a partial image and a second image portion $IM_C$ including the deep blood vessel image $IM_d^*$ as a partial image. Since the first image portion $IM_B$ and the second image portion $IM_C$ include not only the shallow blood vessel image and the deep blood vessel image but also an image of a non-blood vessel portion, by using features of the blood vessel portion with which the blood vessel portion can be distinguished from the non-blood vessel portion, the image of the non-blood vessel portion is removed and the blood vessel image is detected. That is, the detection unit 220a detects the shallow blood vessel image $IM_s^*$ and the deep blood vessel image $IM_d^*$ from the first image portion $IM_B$ and the second image portion $IM_C$ using the features of the blood vessel.

As described above, in the separation illustrated in FIGS. 6(a) and 6(b), the fact that the blood vessel images captured from the first blood vessel detection image $IM_1^*$ and the second blood vessel detection image $IM_2^*$ including the blood vessel image emphasized using the features of the blood vessel are different depending on the wavelength band range of the illumination light (when the wavelength band is on the short wavelength side, it is difficult to image a deep blood vessel compared to the long wavelength side) is used. As a result, the emphasized blood vessel image in the first blood vessel detection image $IM_1^*$ and the second blood vessel detection image $IM_2^*$ can be separated into the region of the shallow blood vessel image $IM_s^*$ and the region of the deep blood vessel image $IM_d^*$.

Furthermore, in the separation illustrated in FIG. 6(c), by using the fact that the blood vessel images captured are different depending on the wavelength band range of the illumination light from the second captured image $IM_2$ obtained by imaging the shallow blood vessel in the vicinity of the surface of the biological tissue and the first captured image $IM_1$ obtained by imaging the shallow blood vessel in the vicinity of the surface of the biological tissue and the deep blood vessel at a certain depth compared to the vicinity of the surface, it is possible to finally separate into the region of the shallow blood vessel image $IM_s^*$ in which the blood vessel image is emphasized and the region of the deep blood vessel image $IM_d^*$ in which the blood vessel image is emphasized.

The feature amount calculation unit 220c calculates the shallow blood vessel feature amount related to the shallow blood vessel image $IM_s^*$ and the deep blood vessel feature amount related to the deep blood vessel image $IM_d^*$. For example, the shallow blood vessel feature amount is a total value or a representative value of pixel values of the second captured image $IM_2$ in the region of the shallow blood vessel image $IM_s^*$, and the deep blood vessel feature amount is, for example, a total value or a representative value of pixel values of the first captured image $IM_1$ in the region of the deep blood vessel image $IM_d^*$. The representative value includes an average value and a median value. In addition, the shallow blood vessel feature amount and the deep blood vessel feature amount may be the sum of the number of pixels in the region of the shallow blood vessel image $IM_s^*$ and the region of the deep blood vessel image $IM_d^*$.

When the shallow blood vessel feature amount and the deep blood vessel feature amount are a total value or a representative value of the pixel values, the separation unit 220b obtains the pixel value of the corresponding region of the second captured image $IM_2$ corresponding to the region of the shallow blood vessel image $IM_s^*$ as the pixel value of the shallow blood vessel image $IM_s^*$. Further, the pixel value of the corresponding region of the first captured image $IM_1$ corresponding to the region of the deep blood vessel image $IM_d^*$ is obtained as the pixel value of the deep blood vessel image $IM_d^*$. The feature amount calculation unit 220c calculates the shallow blood vessel feature amount and the deep blood vessel feature amounts using the obtained pixel value of the shallow blood vessel image $IM_s^*$ and the obtained pixel value of the deep blood vessel image $IM_d^*$. As a result, the severity can be evaluated using the shallow blood vessel feature amount and the deep blood vessel feature amount in consideration of the pixel values.

The calculation of the severity performed by the evaluation unit 220d is not particularly limited as long as the calculation is performed using at least the shallow blood vessel feature amount and the deep blood vessel feature amount. The value of the severity may be, for example, a value obtained by adding or subtracting a value obtained by multiplying the shallow blood vessel feature amount by a predetermined coefficient and a value obtained by multiplying the deep blood vessel feature amount by a predetermined coefficient. In this case, the reference images of the plurality of biological tissues whose severity is known by a doctor or the like may be prepared in advance, and the coefficients may be calculated and obtained in advance by regression analysis using information of the shallow blood vessel feature amounts and the deep blood vessel feature amounts obtained from the reference images and information of the evaluation.

In addition, in a case where the evaluation of the reference image described above is set to one of a plurality of levels, the evaluation unit 220d performs cluster analysis on a set of values of the shallow blood vessel feature amount and the deep blood vessel feature amount obtained from the reference image as a sample, divides the set into a plurality of clusters, and assigns a level that most matches a plurality of samples in the cluster in advance. The evaluation unit 220d may determine to which cluster the calculated values of the shallow blood vessel feature amount and the deep blood vessel feature amount belong, and evaluate the severity as one of the plurality of levels.

According to one embodiment, in addition to the shallow blood vessel feature amount and the deep blood vessel feature amount, a feature amount obtained by quantifying a feature appearing as a lesion of a biological tissue may be included to evaluate the severity. For example, when inflammation such as ulcerative colitis occurs, the severity may be evaluated using feature amounts obtained by quantifying a degree of a red component appearing due to inflammation of a biological tissue in a captured image using white light as illumination light, together with the shallow blood vessel feature amount and the deep blood vessel feature amount.

In addition, according to one embodiment, the evaluation unit 220d may use a prediction model obtained by performing machine learning on a correspondence relationship between the shallow blood vessel feature amount and the deep blood vessel feature amount and the evaluation on the severity of the lesion of the biological tissue, with information on the evaluation of each of a plurality of reference images for which evaluation on the severity prepared in advance has been determined, and the shallow blood vessel feature amount and the deep blood vessel feature amount calculated from the reference image using the image processing unit 220 as machine learning data. In this case, the evaluation unit 220d may predict and evaluate the severity from the value of the shallow blood vessel feature amount and the value of the deep blood vessel feature amount in the biological tissue calculated by the feature amount calculation unit 220c. For machine learning of the predictive model, for example, deep learning by a neural network is used. In addition, a random forest using a tree structure can be used. As the model, a known model such as a convolutional neural network or a stacked autoencoder can be used. By using the prediction model subjected to the machine learning in this manner, it is possible to evaluate the severity with high accuracy.

In this case, the separation unit 220b of the image processing unit 220 separates the biological tissue into a first image portion including the shallow blood vessel image $IM_s^*$ as a part of the image and a second image portion including the deep blood vessel image $IM_d^*$ as a part of the image, which have different depth positions from the surface of the biological tissue.

The detection unit 220a generates the shallow blood vessel image $IM_s^*$ and the deep blood vessel image $IM_d^*$ from the first image portion and the second image portion by using the template matching using the feature shape of the blood vessel.

According to one embodiment, as illustrated in FIG. 4, the detection unit 220a preferably detects and emphasizes the blood vessel image by the template matching using the feature shape of the blood vessel in which the blood vessel extends linearly. Since the shape of the blood vessel can be approximated as a linear shape extending in one direction, it is possible to prepare a template in which the extending direction of the line is different as illustrated in FIG. 4. Therefore, it is possible to accurately detect and emphasize the blood vessel image.

Note that, in the above-described embodiment, the light source device 230 uses the first light and the second light as the illumination light, but may emit three or more lights as the illumination light. When three light beams are used, the third light beam that is the third light beam preferably has a wavelength band on a longer wavelength side than the wavelength band of the first light beam. When the wavelength band of the first light is, for example, 520 nm to 590 nm or 590 nm to 610 nm, and the wavelength band of the second light is, for example, 430 nm to 470 nm or 450 nm to 470 nm, the wavelength band of the third light is, for example, 620 to 650 nm. Since the third captured image obtained by using the third light includes the blood vessel image deeper than the first captured image obtained by using the first light, it is possible to distinguish and separate blood vessel images of blood vessels at different positions in three stages in the depth direction. As described above, by using three or more beams of light having different wavelength bands as the illumination light, it is possible to distinguish and separate the blood vessel images of the blood vessels at different positions having three or more levels of depth.

The endoscope system of the present invention is described above in detail, but the endoscope system of the present invention is not limited to the above-described embodiment, and may of course be modified or altered in various ways in a range not deviating from the scope and spirit of the present invention.

REFERENCE SIGNS LIST

1 Endoscope system
100 Electronic scope
102 LCB
104 Light distribution lens
106 Objective lens
108 Image sensor
108a IR cut filter
108b Color filter
112 Driver signal processing circuit
114 Memory
200 Electronic endoscope processor
202 System controller
204 Memory
206 Timing controller
208 Operation panel
210 NIC
220 Image processing unit
220a Detection unit
220b Separation unit
220c Feature amount calculation unit
220d Evaluation unit
224 Memory
230 Light source unit
300 Monitor
400 Printer
600 Server

The invention claimed is:
1. An endoscope system, comprising:
a light source device configured to emit illumination light;
an electronic endoscope configured to image a biological tissue including a blood vessel portion and a non-blood vessel portion in a body cavity illuminated with the illumination light;
a processor that includes an image processing unit configured to calculate a severity of a lesion of the biological tissue from an image of the biological tissue obtained by the electronic endoscope by using information of the image; and
a monitor configured to display information on the severity of the lesion, wherein
the light source device is configured to emit, as at least the illumination light, first light and second light having a wavelength band having a shorter wavelength than a wavelength band of the first light, and
the image processing unit includes
a detection unit configured to
generate a first blood vessel detection image including a first emphasized blood vessel image from a first captured image obtained by illumination with the first light, and
further generate a second blood vessel detection image including a second emphasized blood vessel image from a second captured image obtained by illumination with the second light,
by using features of the blood vessel portion with which the blood vessel portion is able to be distinguished from the non-blood vessel portion, a separation unit configured to separate, from the first blood vessel detection image and the second blood vessel detection image, blood vessel images in the first blood vessel detection image and the second blood vessel detection image into a shallow blood vessel image and a deep blood vessel image as blood vessel images having different depth positions from a surface of the biological tissue; and a feature amount calculation unit configured to calculate a shallow blood vessel feature amount of the shallow blood vessel image and a deep blood vessel feature amount of the deep blood vessel image, wherein the image processing unit is configured to calculate the severity of the lesion of the biological tissue using at least the shallow blood vessel feature amount and the deep blood vessel feature amount.

2. The endoscope system according to claim 1, wherein the separation unit detects a region of a blood vessel image in the second blood vessel detection image as a region of the shallow blood vessel image, and detects a region of the blood vessel image in the second blood vessel detection image as a region of the deep blood vessel image by removing the detected region of the shallow blood vessel image from a region of the blood vessel image in the first blood vessel detection image to thereby detect the shallow blood vessel image and the deep blood vessel image.

3. The endoscope system according to claim 2, wherein the separation unit is configured to obtain a pixel value of a corresponding region of the second captured image corresponding to the region of the shallow blood vessel image as a pixel value of the shallow blood vessel image, and to obtain a pixel value of a corresponding region of the first captured image corresponding to the region of the deep blood vessel image as a pixel value of the deep blood vessel image, and the feature amount calculation unit is configured to calculate the shallow blood vessel feature amount and the deep blood vessel feature amount using the obtained pixel value of the shallow blood vessel image and the obtained pixel value of the deep blood vessel image.

4. The endoscope system according to claim 1, wherein the separation unit is configured to detect a region of the shallow blood vessel image according to whether or not each pixel value of an average detection image is equal to or greater than a preset first threshold value, each pixel value of the average detection image being an average value of pixel values of corresponding pixels of the first blood vessel detection image and the second blood vessel detection image, to detect a mixed region including a region of the shallow blood vessel image and a region of the deep blood vessel image according to whether or not each pixel value of the first captured image is equal to or greater than a preset second threshold value, and to detect a region of the deep blood vessel image by removing the detected region of the shallow blood vessel image from the detected mixed region.

5. The endoscope system according to claim 1, wherein the detection unit is configured to detect a blood vessel image emphasized by template matching using a feature shape of a blood vessel extending linearly.

6. The endoscope system according to claim 1, wherein the image processing unit is configured to calculate the severity of the lesion by adding or subtracting a value obtained by multiplying the value of the shallow blood vessel feature amount by a first coefficient and a value obtained by multiplying the value of the deep blood vessel feature amount by a second coefficient.

7. The endoscope system according to claim 1, wherein the image processing unit is configured to perform a predictive evaluation on the severity of the lesion from a value of the shallow blood vessel feature amount and a value of the deep blood vessel feature amount in the biological tissue, which are calculated by the feature amount calculation unit by using a prediction model obtained by performing machine learning on a correspondence relationship between the shallow blood vessel feature amount and the deep blood vessel feature amount and the evaluation on the severity of the lesion of the biological tissue, with determined information on an evaluation of each of a plurality of reference images for which evaluation on the severity of the lesion is prepared in advance, and wherein the shallow blood vessel feature amount and the deep blood vessel feature amount are calculated from the plurality of reference images as machine learning data using the image processing unit.

8. The endoscope system according to claim 1, wherein the light source device is configured to emit one light, which includes each of the first light and the second light as a light component, as the illumination light, and the electronic endoscope is configured to separate an object image of the biological tissue into the first captured image and the second captured image using an optical filter.

9. The endoscope system according to claim 1, wherein the first light includes a first absorption peak wavelength among a plurality of absorption peak wavelengths of hemoglobin in a wavelength band, and the second light includes, in a wavelength band, a second absorption peak wavelength a shorter than the first absorption peak wavelength among the plurality of absorption peaks.

10. The endoscope system according to claim 1, wherein a wavelength band of at least one of the first light and the second light does not include any of a plurality of absorption peak wavelengths of hemoglobin.

11. The endoscope system according to claim 1, wherein the wavelength band of the second light includes a wavelength having an absorption coefficient of hemoglobin greater than a maximum value of an absorption coefficient of hemoglobin in the wavelength band of the first light.

12. The endoscope system according to claim 1, wherein the light source device is configured to emit third light having a wavelength band of a longer wavelength than a wavelength band of the first light.

13. An endoscope system, comprising:

a light source device configured to emit illumination light;

an electronic endoscope configured to image a biological tissue including a blood vessel portion and a non-blood vessel portion in a body cavity illuminated with the illumination light;

a processor that includes an image processing unit configured to calculate a severity of a lesion of the biological tissue from an image of the biological tissue obtained by the electronic endoscope by using information of the image; and a monitor configured to display information on the severity of the lesion, wherein the light source device is configured to emit, as at least the illumination light, first light and second light having a wavelength band having a shorter wavelength than a wavelength band of the first light, and the image processing unit includes a separation unit configured to separate and extract, from a first captured image obtained by illumination with the first light and a second captured image obtained by illumination with the second light, a first image portion including a shallow blood vessel image as a part of an image and a second image portion including a deep blood vessel image as a part of an image, among the shallow blood vessel image and the deep blood vessel image with different depth positions from a surface of the biological tissue, a detection unit configured to generate the shallow blood vessel image and the deep blood vessel image from the first image portion and the second image portion by using features of the blood vessel portion with which the blood vessel portion is able to be distinguished from the non-blood vessel portion, and a feature amount calculation unit configured to calculate a value of a shallow blood vessel feature amount of the shallow blood vessel image and a value of a deep blood vessel feature amount of the deep blood vessel image, wherein the image processing unit is configured to calculate the severity of the lesion of the biological tissue using at least the value of the shallow blood vessel feature amount and the value of the deep blood vessel feature amount.

14. The endoscope system according to claim 13, wherein the separation unit is configured to create the first image portion according to whether or not each pixel value of an average image value is equal to or greater than a preset first threshold value, each pixel value of the average detection image being an average value of pixel values of corresponding pixels of the first captured image and the second captured image, to detect a mixed image including the shallow blood vessel image and the deep blood vessel image as a part of images according to whether or not each pixel value of the first captured image is a preset second threshold value, and to remove the generated first image portion from the detected mixed image to create the second image portion.

* * * * *